United States Patent
Cohen et al.

(10) Patent No.: US 10,786,166 B2
(45) Date of Patent: Sep. 29, 2020

(54) MAPPING OF ACTIVATION WAVEFRONTS

(71) Applicant: Biosense Webster (Israel) Ltd., Yokneam (IL)

(72) Inventors: Assaf Cohen, Kiryat Bialik (IL); Meir Bar-Tal, Haifa (IL); Elad Nakar, Timrat (IL); Ido Ilan, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 129 days.

(21) Appl. No.: 16/160,062

(22) Filed: Oct. 15, 2018

(65) Prior Publication Data

US 2020/0113465 A1    Apr. 16, 2020

(51) Int. Cl.
  *A61B 5/04*    (2006.01)
  *A61B 5/00*    (2006.01)
  *A61B 5/042*   (2006.01)

(52) U.S. Cl.
  CPC ........ *A61B 5/04011* (2013.01); *A61B 5/0422* (2013.01); *A61B 5/742* (2013.01)

(58) Field of Classification Search
  CPC . A61B 5/04011; A61B 5/7225; A61B 5/7235; A61B 5/742; G06T 13/00–80
  See application file for complete search history.

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 2005/0154281 A1* | 7/2005 | Xue ............ A61B 6/5247 600/407 |
| 2014/0058282 A1 | 2/2014 | O'Grady |
| 2015/0228254 A1 | 8/2015 | Olson |
| 2017/0055864 A1 | 3/2017 | Han et al. |

(Continued)

OTHER PUBLICATIONS

European Search Report for corresponding EPA No. 19202997.3 dated Jan. 29, 2020.

(Continued)

*Primary Examiner* — Daniel F Hajnik

(57) ABSTRACT

In one embodiment, a cardiac mapping system includes a medical examination device to capture data over time at multiple sample locations over a surface of at least one chamber of a heart, a display screen, and processing circuitry to process the captured data to determine a description of a propagation of activation wavefronts associated with activation times over the surface of the at least one chamber of the heart, calculate activation wavefront propagation path traces wherein each path trace describes a point on one activation wavefront being propagated over the surface of the at least one chamber of the heart according to an advancement of the activation wavefront such that the path traces describe the propagation of different points according to corresponding activation wavefronts, prepare a visualization showing the path traces on a representation of the at least one chamber, and render the visualization to the display screen.

26 Claims, 10 Drawing Sheets

(56) References Cited

U.S. PATENT DOCUMENTS

2017/0281031 A1* 10/2017 Houben .............. A61B 18/12
2017/0311833 A1   11/2017 Afonso et al.

OTHER PUBLICATIONS

Gnus Holm et al: "A New Method for Analysis of Atrial Activation During Chronic Atrial Fibrillation in Man", IEEE Transactions on Biomedical Engineering, vol. 43, No. 2, Feb. 1, 1996.
Ney Caroline H et al: "Rotor Tracking Using Phase of Electrograms Recorded During Atrial Fibrillation", Annals of Biomedical Engineering, vol. 45, No. 4, pp. 910-923, Dec. 5, 2016.
Lammers W J E P et al: "The initiation, continuation, and termination of spontaneous episodes of circus movements in the pregnant myometrium of the rat", American Journal of Obstetrics & Gynecology, vol. 179, No. 6, pp. 1515-1526, Dec. 1, 1998.

* cited by examiner

MAPPING OF ACTIVATION WAVEFRONTS

FIELD OF THE INVENTION

The present invention relates to mapping cardiac electrical activity, and in particular, but not exclusively to, mapping of activation wavefronts.

BACKGROUND

By way of introduction, maps of cardiac electrical activity are typically presented by overlaying different colors for the different local activation times (LATs) on a representation of the heart.

US Published Patent Application 2017/0055864 describes a map of cardiac activation wavefronts that can be created from a plurality of mesh nodes, each of which is assigned a conduction velocity vector. The cardiac activation wavefronts can be displayed on a graphical representation of the cardiac geometry.

US Published Patent Application 2017/0311833 describes a system for diagnosing arrhythmias and directing catheter therapies that may allow for measuring, classifying, analyzing, and mapping spatial electrophysiological (EP) patterns within a body. The system may also use an electronic control system for computing and providing the user with a variety of metrics, derivative metrics, high definition (HD) maps, HD composite maps, and general visual aids for association with a geometrical anatomical model shown on a display device.

US Published Patent Application 2015/0228254 describes a method of generating an anatomical map that includes acquiring geometry information and biological information for an anatomical region. The geometry and biological information are associated with each other, for example by associating measured biological attributes with the anatomical locations at which they were measured. A graphical representation of the anatomical region, including a map of at least two biological attributes, can then be superimposed upon a geometric model of the anatomical region. The map can be a blended map and/or can utilize glyphs to represent the displayed biological attributes.

U.S. Pat. No. 6,301,496 describes a method of diagnosing an abnormal condition in a biological structure, such as the heart, including the steps of measuring a physiological response at at least three sampled points on a surface of the biological structure, calculating a vector function related to the response, displaying a representation of the vector function, and inferring the abnormal condition from the representation. The method is said to be particularly useful for diagnosing cardiac arrhythmias, in which case the physiological response is a voltage, from which is inferred a local activation time and the vector function is a gradient of the local activation time, specifically, a conduction velocity.

SUMMARY

There is provided in accordance with an embodiment of the present disclosure, a cardiac mapping system including a medical examination device to capture data over time at multiple sample locations over a surface of at least one chamber of a heart, a display screen, and processing circuitry configured to process the captured data to determine a description of a propagation of activation wavefronts associated with a plurality of activation times over the surface of the at least one chamber of the heart, calculate a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart an advancement of the one activation wavefront such that the plurality of activation wavefront propagation path traces describe the propagation of a plurality of different points corresponding ones of the activation wavefronts, prepare a visualization showing the plurality of activation wavefront propagation path traces on a representation of the at least one chamber of the heart, and render the visualization to the display screen.

Further in accordance with an embodiment of the present disclosure the visualization is an animated visualization, and the processing circuitry is operative to prepare the animated visualization showing a growth of the plurality of activation wavefront propagation path traces on the representation of the at least one chamber of the heart the advancement of the activation wavefronts over the surface.

Still further in accordance with an embodiment of the present disclosure the processing circuitry is configured to animate the growth of the one activation wavefront propagation path trace in the animated visualization by moving the point of the one activation wavefront propagation path trace a direction of movement of the one activation wavefront at a current location of the point.

Additionally, in accordance with an embodiment of the present disclosure the processing circuitry is configured to calculate a speed of the growth of the one activation wavefront propagation path trace as a function of a speed of movement of the one activation wavefront at the current location of the point.

Moreover in accordance with an embodiment of the present disclosure the processing circuitry is configured to select, in a random or a pseudo-random manner, a plurality of start locations on the representation of the at least one chamber of the heart, assign the plurality of start locations as start positions of the plurality of activation wavefront propagation path traces from which to commence the respective activation wavefront propagation path traces, the one activation wavefront propagation path trace being assigned one start position of the start positions, and animate the growth of each one activation wavefront propagation path trace of the plurality of activation wavefront propagation path traces from the one start position to an end position.

Further in accordance with an embodiment of the present disclosure the processing circuitry is configured to commence the animation of the growth of the plurality of activation wavefront propagation path traces from the start positions at substantially a same time.

Still further in accordance with an embodiment of the present disclosure the processing circuitry is configured, for each one activation wavefront propagation path trace of the plurality of activation wavefront propagation path traces, to animate the one activation wavefront propagation path trace from the one start position to the end position in a cyclical manner.

Additionally, in accordance with an embodiment of the present disclosure the processing circuitry is configured to add a head indicator at the front of each one activation wavefront propagation path trace of the plurality of activation wavefront propagation path traces.

Moreover, in accordance with an embodiment of the present disclosure the processing circuitry is configured to add an indicator to one of the plurality of activation wavefront propagation path traces to indicate a non-conductive area of the at least one chamber of the heart.

Further in accordance with an embodiment of the present disclosure the medical examination device is a probe configured to capture electrical potentials over time at the multiple sample locations over the surface of the at least one chamber of the heart.

Still further in accordance with an embodiment of the present disclosure the processing circuitry is configured to prepare a vector map including a plurality of velocity vectors describing the propagation of the activation wavefronts, prepare an animated visualization showing a growth of the plurality of activation wavefront propagation path traces on the representation of the at least one chamber of the heart the advancement of the activation wavefronts over the surface, and animate each one activation wavefront propagation path trace of the plurality of activation wavefront propagation path traces by moving the point of the one activation wavefront propagation path trace a first plurality of times a first direction of a first vector of the plurality of velocity vectors and then continuing moving the point of the one activation wavefront a second plurality of times a second direction of a second vector of the plurality of velocity vectors.

There is also provided in accordance with still another embodiment of the present disclosure a cardiac mapping method including capturing data over time at multiple sample locations over a surface of at least one chamber of a heart, processing the captured data to determine a description of a propagation of activation wavefronts associated with a plurality of activation times over the surface of the at least one chamber of the heart, calculating a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart an advancement of the one activation wavefront such that the plurality of activation wavefront propagation path traces describe the propagation of a plurality of different points corresponding ones of the activation wavefronts, preparing a visualization showing the plurality of activation wavefront propagation path traces on a representation of the at least one chamber of the heart, and rendering the visualization to a display screen.

Additionally, in accordance with an embodiment of the present disclosure the visualization is an animated visualization, and the method further includes preparing the animated visualization showing a growth of the plurality of activation wavefront propagation path traces on the representation of the at least one chamber of the heart the advancement of the activation wavefronts over the surface.

Moreover, in accordance with an embodiment of the present disclosure the preparing the animated visualization includes moving the point of the one activation wavefront propagation path trace a direction of movement of the one activation wavefront at a current location of the point.

Further in accordance with an embodiment of the present disclosure, the method includes calculating a speed of the growth of the one activation wavefront propagation path trace as a function of a speed of movement of the one activation wavefront at the current location of the point.

Still further in accordance with an embodiment of the present disclosure, the method includes selecting, in a random or a pseudo-random manner, a plurality of start locations on the representation of the at least one chamber of the heart, assigning the plurality of start locations as start positions of the plurality of activation wavefront propagation path traces from which to commence the respective activation wavefront propagation path traces, the one activation wavefront propagation path trace being assigned one start position of the start positions, and animating the growth of each one activation wavefront propagation path trace of the plurality of activation wavefront propagation path traces from the one start position to an end position.

Additionally, in accordance with an embodiment of the present disclosure, the method includes commencing the animation of the growth of the plurality of activation wavefront propagation path traces from the start positions at substantially a same time.

Moreover, in accordance with an embodiment of the present disclosure, the method includes, for each one activation wavefront propagation path trace of the plurality of activation wavefront propagation path traces, animating the one activation wavefront propagation path trace from the one start position to the end position in a cyclical manner.

Further in accordance with an embodiment of the present disclosure, the method includes adding a head indicator at the front of each one activation wavefront propagation path trace of the plurality of activation wavefront propagation path traces.

Still further in accordance with an embodiment of the present disclosure, the method includes adding an indicator to one of the plurality of activation wavefront propagation path traces to indicate a non-conductive area of the at least one chamber of the heart.

Additionally in accordance with an embodiment of the present disclosure, the method includes preparing a vector map including a plurality of velocity vectors describing the propagation of the activation wavefronts, preparing an animated visualization showing a growth of the plurality of activation wavefront propagation path traces on the representation of the at least one chamber of the heart the advancement of the activation wavefronts over the surface, and animating each one activation wavefront propagation path trace of the plurality of activation wavefront propagation path traces by moving the point of the one activation wavefront propagation path trace a first plurality of times a first direction of a first vector of the plurality of velocity vectors and then continuing moving the point of the one activation wavefront a second plurality of times a second direction of a second vector of the plurality of velocity vectors.

There is also provided in accordance with still another embodiment of the present disclosure a cardiac visualization system including a memory to store a description of a propagation of activation wavefronts associated with a plurality of activation times over a surface of at least one chamber of a heart, and processing circuitry configured to process the captured data to determine a description of a propagation of activation wavefronts associated with a plurality of activation times over the surface of the at least one chamber of the heart, calculate a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart an advancement of the one activation wavefront such that the plurality of activation wavefront propagation path traces describe the propagation of a plurality of different points corresponding ones of the activation wavefronts, prepare a visualization showing the plurality of activation wavefront propagation path traces on a representation of the at least one chamber of the heart, and render the visualization to a display screen.

Moreover, in accordance with an embodiment of the present disclosure the visualization is an animated visualization, and the processing circuitry is operative to prepare the animated visualization showing a growth of the plurality of activation wavefront propagation path traces on the representation of the at least one chamber of the heart the advancement of the activation wavefronts over the surface.

Further in accordance with an embodiment of the present disclosure the processing circuitry is configured to animate the growth of the one activation wavefront propagation path trace in the animated visualization by moving the point of the one activation wavefront propagation path trace a direction of movement of the one activation wavefront at a current location of the point.

Still further in accordance with an embodiment of the present disclosure the processing circuitry is configured to calculate a speed of the growth of the one activation wavefront propagation path trace as a function of a speed of movement of the one activation wavefront at the current location of the point.

Additionally in accordance with an embodiment of the present disclosure the processing circuitry is configured to select, in a random or a pseudo-random manner, a plurality of start locations on the representation of the at least one chamber of the heart, assign the plurality of start locations as start positions of the plurality of activation wavefront propagation path traces from which to commence the respective activation wavefront propagation path traces, the one activation wavefront propagation path trace being assigned one start position of the start positions, and animate the growth of each one activation wavefront propagation path trace of the plurality of activation wavefront propagation path traces from the one start position to an end position.

There is also provided in accordance with still another embodiment of the present disclosure a cardiac visualization method including storing a description of a propagation of activation wavefronts associated with a plurality of activation times over a surface of at least one chamber of a heart, processing the captured data to determine a description of a propagation of activation wavefronts associated with a plurality of activation times over the surface of the at least one chamber of the heart, calculating a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart an advancement of the one activation wavefront such that the plurality of activation wavefront propagation path traces describe the propagation of a plurality of different points corresponding ones of the activation wavefronts, preparing a visualization showing the plurality of activation wavefront propagation path traces on a representation of the at least one chamber of the heart, and rendering the visualization to a display screen.

Moreover, in accordance with an embodiment of the present disclosure the visualization is an animated visualization, and the method further includes preparing the animated visualization showing a growth of the plurality of activation wavefront propagation path traces on the representation of the at least one chamber of the heart the advancement of the activation wavefronts over the surface.

Further in accordance with an embodiment of the present disclosure, the method includes animating the growth of the one activation wavefront propagation path trace in the animated visualization by moving the point of the one activation wavefront propagation path trace a direction of movement of the one activation wavefront at a current location of the point.

Still further in accordance with an embodiment of the present disclosure, the method includes calculating a speed of the growth of the one activation wavefront propagation path trace as a function of a speed of movement of the one activation wavefront at the current location of the point.

Additionally in accordance with an embodiment of the present disclosure, the method includes selecting, in a random or a pseudo-random manner, a plurality of start locations on the representation of the at least one chamber of the heart, assigning the plurality of start locations as start positions of the plurality of activation wavefront propagation path traces from which to commence the respective activation wavefront propagation path traces, the one activation wavefront propagation path trace being assigned one start position of the start positions, and animating the growth of each one activation wavefront propagation path trace of the plurality of activation wavefront propagation path traces from the one start position to an end position.

There is also provided in accordance with still another embodiment of the present disclosure a software product, including a non-transient computer-readable medium in which program instructions are stored, which instructions, when read by a central processing unit (CPU), cause the CPU to store a description of a propagation of activation wavefronts associated with a plurality of activation times over a surface of at least one chamber of a heart, calculate a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart an advancement of the one activation wavefront such that the plurality of activation wavefront propagation path traces describe the propagation of a plurality of different points corresponding ones of the activation wavefronts, prepare a visualization showing the plurality of activation wavefront propagation path traces on a representation of the at least one chamber of the heart, and render the visualization to the display screen.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
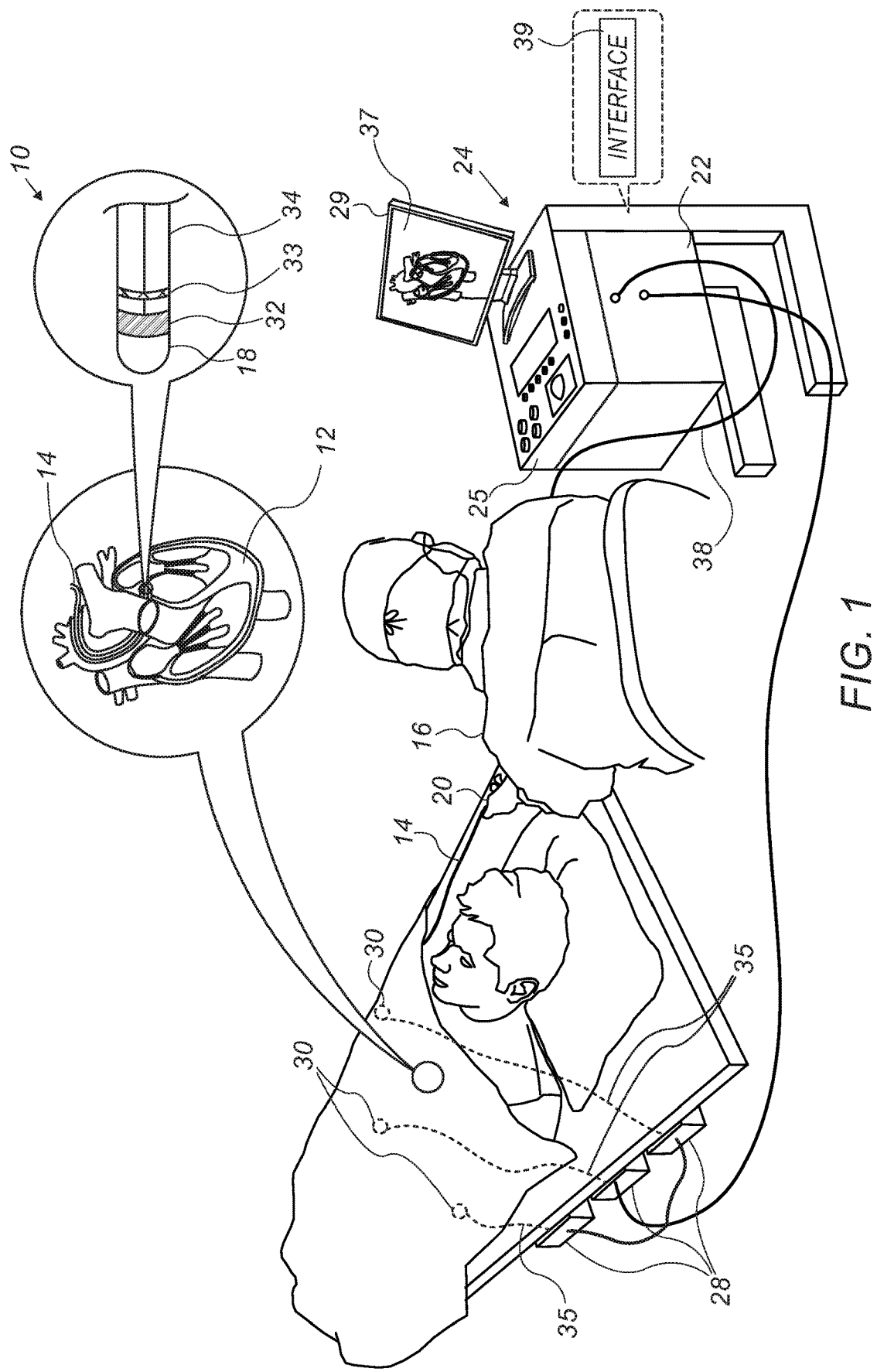
FIG. 1 is a partly pictorial, partly block diagram view of a cardiac mapping system constructed and operative in accordance with an embodiment of the present invention.

By way of introduction, maps of cardiac electrical activity are typically presented by overlaying different colors for the corresponding to different local activation times (LATs) on a representation of the heart. However, deriving medical information from these maps may be mentally demanding.

Embodiments of the present invention provide a map of cardiac electrical activity showing how cardiac electrical activity flows over the representation of the heart using an intuitive (static or animated) three-dimensional (3D) visualization including activation wavefront propagation path traces. The activation wavefront propagation path traces indicate a direction of movement of activation wavefronts associated with a plurality of activation times over the surface of at least one chamber of the heart. A growth of the activation wavefront propagation path traces may also be animated according to a speed of the activation wavefronts. The activation wavefront propagation path traces enable easy derivation of medical information from the maps, such as identification of non-conductive areas and other propagation related issues such as circular activity, by way of example only.

In a data capture stage, underlying cardiac activity is captured using a medical examination device to capture data over time at multiple sample locations over the surface of the chamber(s) of the heart. The captured data is processed to determine a description of the propagation of the activation wavefronts associated with the activation times over the surface of the chamber(s) of the heart. The medical examination device may include a probe to capture electrical cardiac activity. Additionally, or alternatively, body surface vests may be used to estimate the propagation of the activation wavefronts. Additionally, or alternatively, an inter-cardiac and/or trans-thoracic ultrasound-based system may be used to estimate mechanical wavefronts.

The description of the propagation of the activation wavefronts may be represented using any suitable representation, for example, but not limited to, a spline function or as a vector map including velocity vectors describing the propagation of the activation wavefronts associated with the activation times. It should be carefully noted that a velocity vector simply describes the velocity of an activation wavefront at a single point and does not describe any path of propagation. Therefore, the wavefront propagation path traces cannot be described as long velocity vectors.

Using the description of the propagation of the activation wavefronts, a static visualization may be prepared on a computer display, showing the activation wavefront propagation path traces on a representation of the chamber(s) of the heart. When the visualization is animated, the visualization may show a growth of the activation wavefront propagation path traces on the representation of the chamber(s) of the heart according to the advancement of the activation wavefronts over the surface. The static and/or animated visualization may show a rotation of the three-dimensional representation of the chamber(s) of the heart.

As part of an initialization process in order to generate this visualization, start positions of the activation wavefront propagation path traces may be assigned randomly, pseudo-randomly, or according to a given pattern, over the 3D representation of the chamber(s) of the heart. A density of the start positions may be user-configurable.

Each activation wavefront propagation path trace is calculated so that it describes a point on one activation wavefront of the activation wavefronts being propagated from its start position over the surface of the chamber(s) of the heart according to an advancement of that activation wavefront. Therefore, the activation wavefront propagation path traces describe the propagation of different points with different corresponding start positions according to corresponding activation wavefronts.

The direction(s) that each activation wavefront propagation path trace follows is determined according to a direction of movement of the one activation wavefront at a current location of the point being propagated. Similarly, when the visualization is animated, the speed of growth of each activation wavefront propagation path trace is a function of a speed of movement of the activation wavefront at the current location of the point being propagated. In one example using velocity vectors, the point which is being propagated is moved multiple times according to a velocity vector associated with the current location of the point and is then moved another multiple times according to a different velocity vector associated with a new location of the point, and so on.

The point may be propagated according to a given time period or a given distance over the surface of the chamber(s) of the heart thereby defining an end position of the associated activation wavefront propagation path trace according to the given time period or given distance. When the visualization is animated and an activation wavefront propagation path trace reaches the end of its path, the path trace may then be removed from the visualization and start growing again from its start position according to the speed of its activation wavefront. This may be repeated in a cyclical manner.

In accordance with some embodiments, the propagation of a point may be calculated based on the following formula: $L_N = L_c + \bar{v} \cdot \Delta t$, where $L_N$ is the next location of the point being propagated, $L_c$ is the current location of the point being propagated, $\bar{v}$ is a velocity vector from the description of the propagation of the activation wavefronts (e.g., from a function describing the propagation of the activation wavefronts) associated with the current location of the point, and $\Delta t$ is a time value, which may be user configurable in order to increase and decrease the granularity of the movement of the point being propagated. When the visualization is animated, adjusting $\Delta t$ may be used to adjust the speed of the animation.

A visible head is generally added at the front of each activation wavefront propagation path trace to emphasize the direction of movement of the activation wavefront propagation path trace. The visible head provides a useful direction indicator whether the visualization is static or animated. The visible head is generally thicker than the rest of the activation wavefront propagation path trace. A format (e.g., color, shading and/or pattern) and/or a size (e.g., length and/or width) of each activation wavefront propagation path trace may indicate a magnitude of the underlying velocity of the activation wavefront. For example, a darker color may indicate a faster travelling trace associated with a higher speed wavefront.

Optionally, an indicator may be added to an activation wavefront propagation path trace to indicate a non-conductive area of the chamber(s) of the heart in the visualization.

In some embodiments, user interaction with the visualization may enable a user to initiate an action corresponding to a position which was selected by a user on the representation of the chamber(s) of the heart. The action may include any suitable action, for example, but not limited to, displaying additional information about the selected position, outputting a control command to perform an ablation at the selected position, outputting a control command to perform further investigation at the selected position; and/or adding an annotation at the selected position. Automatic analysis of the visualization may result in any suitable action, for example, but not limited to, outputting a control command to perform an ablation at a given position, outputting a control command to perform further investigation at a given position.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

System Description

Turning now to the drawings, reference is initially made to FIG. 1, which is a pictorial illustration of a cardiac mapping system 10, constructed and operative in accordance with a disclosed embodiment of the invention, for evaluating electrical activity and optionally for performing ablative procedures on a heart 12 of a living subject. The system comprises a probe 14, such as a catheter, which is percutaneously inserted by an operator 16 through the patient's vascular system into a chamber or vascular structure of the heart 12. The operator 16, who is typically a physician, brings a distal tip 18 of the probe 14 into contact with the heart wall, for example, at an ablation target site or to capture electrical potentials over time at multiple sample location over a surface of one or more chambers of the heart 12. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 33 Technology Drive, Irvine, Calif. 92618 USA. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the probe to one or more electrodes at the distal tip 18, which apply the radiofrequency energy to the myocardium. The energy is absorbed in the tissue, heating it to a temperature (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The probe 14 typically comprises a handle 20, having suitable controls on the handle to enable the operator 16 to steer, position and orient the distal tip 18 of the probe 14 as desired for the ablation. To aid the operator 16, a distal portion of the probe 14 contains position sensors (not shown) that provide signals to processing circuitry 22, located in a console 24. The processing circuitry 22 may fulfill several processing functions as described below.

Ablation energy and electrical signals can be conveyed to and from the heart 12 through one or more ablation electrodes 32 located at or near the distal tip 18 via cable 34 to the console 24. In such a manner, the ablation electrodes 32 are configured to capture electrical potentials over time at multiple sample location over a surface of one or more chambers of the heart 12. Additionally, or alternatively, other electrodes may be configured to capture electrical potentials over time at multiple sample location over a surface of one or more chambers of the heart 12. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34. The probe 14 may be implemented without the ablation electrodes 32 as an exploratory device having electrodes configured to capture electrical potentials over time at multiple sample location over a surface of one or more chambers of the heart 12.

Wire connections 35 link the console 24 with body surface electrodes 30 and other components of a positioning sub-system for measuring location and orientation coordinates of the probe 14. The processing circuitry 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A sensor for bioelectric information, e.g., a temperature sensor (not shown), typically a thermocouple or thermistor, may be mounted on or near each of the electrodes 32.

The console 24 typically contains one or more ablation power generators 25. The probe 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the probe 14 by generating magnetic fields in a predefined working volume and sensing these fields at the probe 14, using field generating coils 28. The positioning subsystem is described in U.S. Pat. No. 7,756,576, which is hereby incorporated by reference, and in the above-noted U.S. Pat. No. 7,536,218.

As noted above, the probe 14 is coupled to the console 24, which enables the operator 16 to observe and regulate the functions of the probe 14. The processing circuitry 22 may be embodied as a computer with appropriate signal processing circuits. The processing circuitry 22 is coupled to drive a monitor 29 including a display screen 37. The signal processing circuits typically receive, amplify, filter and digitize signals from the probe 14, including signals generated by sensors such as electrical, temperature and contact force sensors, and a plurality of location sensing electrodes (not shown) located distally in the probe 14. The digitized signals are received and used by the console 24 and the positioning system to compute the position and orientation of the probe 14, and to analyze the electrical signals from the electrodes.

In order to generate electroanatomic maps, the processing circuitry 22 typically comprises an electroanatomic map generator, an image registration program, an image or data analysis program and a graphical user interface configured to present graphical information on the monitor 29.

In practice, some or all of these functions of the processing circuitry 22 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The console 24 may also include an interface 39 to receive input commands from the operator 16 via any suitable user input device, for example, but not limited to, a pointing device (such as a mouse of stylus), a keyboard, and/or a touch sensitive screen implemented in the display screen 37.

Typically, the system 10 includes other elements, which are not shown in the figures for the sake of simplicity. For example, the system 10 may include an electrocardiogram (ECG) monitor, coupled to receive signals from the body surface electrodes 30, in order to provide an ECG synchronization signal to the console 24. As mentioned above, the system 10 typically also includes a reference position sensor, either on an externally applied reference patch attached to the exterior of the subject's body, or on an internally placed probe, which is inserted into the heart 12 maintained in a fixed position relative to the heart 12. Conventional pumps and lines for circulating liquids through the probe 14 for cooling the ablation site are provided. The system 10 may receive image data from an external imaging modality, such as an MRI unit or the like and includes image processors that can be incorporated in or invoked by the processing circuitry 22 for generating and displaying images.

Figure 2:
FIGS. 2-5 are various views of cardiac images showing activation wavefront propagation path traces on a representation of at least one chamber of a heart generated by the system of FIG. 1 in accordance with an embodiment of the present invention.
Figure 3:
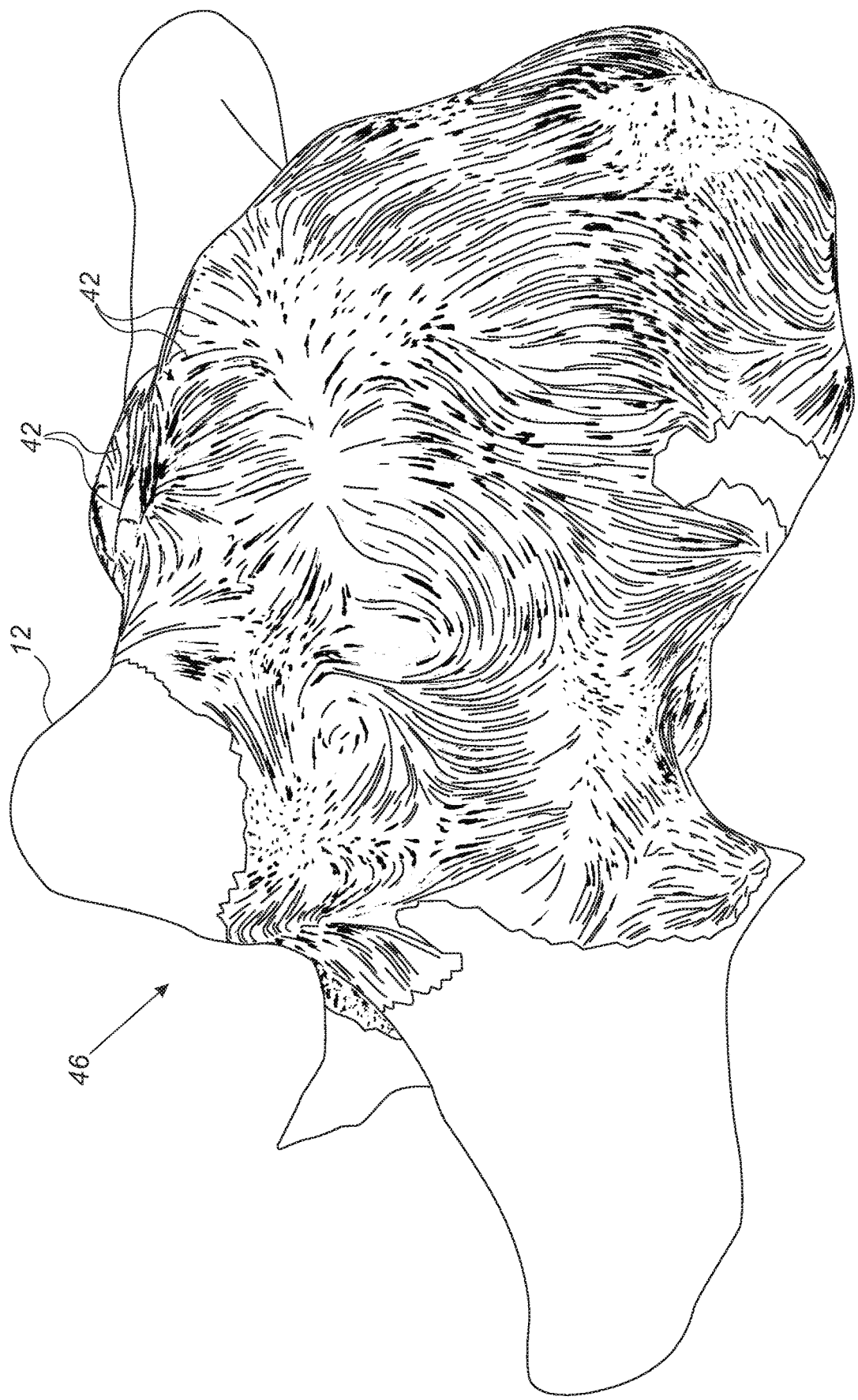
Figure 4:
Figure 5:

Reference is now made to FIGS. 2-5, which are various views of cardiac images showing a plurality of activation wavefront propagation path traces 42 on a representation of one or more chambers of the heart 12 generated by the system 10 of FIG. 1 in accordance with an embodiment of the present invention. FIG. 2 shows the heart 12 viewed from one angle, while FIGS. 3-5 show the heart 12 viewed from a different angle.

The processing circuitry 22 (FIG. 1) is configured prepare a (static or animated) visualization 46 showing activation wavefront propagation path traces 42 on a 3D representation of the chamber(s) of the heart 12. The processing circuitry 22 is configured to render the visualization 46 to the display screen 37 (FIG. 1). The preparation of the visualization 46 is described in more detail with respect to FIGS. 7-12. The format of the visualization 46 is now described in more detail with respect to FIGS. 2-5.

FIGS. 2-5 show the activation wavefront propagation path traces 42 at various stages of growth on the representation of the chamber(s) of the heart 12. For the sake of simplicity only some of the activation wavefront propagation path traces 42 have been labeled. FIGS. 3-5 show the state of growth of the activation wavefront propagation path traces 42 at different times illustrating that the activation wavefront propagation path traces 42 grow when the visualization 46 is animated.

It should be noted that some of the activation wavefront propagation path traces 42 included in the visualization 46 may continue along a surface of the chamber(s) of the heart which is not currently in view on the visualization 46. When the visualization 46 is animated, these activation wavefront propagation path traces 42 may continue to the end of their path (on the surface which is not in view) and once the activation wavefront propagation path traces 42 grow to the end of their respective path, the activation wavefront propagation path traces 42 may be removed from the visualization 46 and start growing again from the beginning of their respective paths which are currently in view. Similarly, activation wavefront propagation path traces 42 which start their paths on a surface of the heart 12 which is currently not in view may appear on the surface currently in view at a later time. In other words, the activation wavefront propagation path traces 42 are generally calculated for one or more chambers of the heart 12 whether or not the surface of the chamber(s) of the heart 12 will be in view in the visualization 46 at any one time.

The processing circuitry 22 (FIG. 1) is configured to prepare the visualization 46 showing a rotation of the three-dimensional representation of the chamber(s) of the heart 12. The visualization 46 may be manipulated by the operator 16 (FIG. 1) to be rotated to any suitable viewing angle. The processing circuitry 22 may also be configured to prepare the visualization 46 as a video which may be played showing the rotation of the three-dimensional representation of the chamber(s) of the heart 12 and/or the growing of the activation wavefront propagation path traces 42 along their respective paths.

The interface 39 (FIG. 1) may be configured to receive a user input selecting a position on the representation of the chamber(s) of the heart 12 in the visualization 46. The processing circuitry 22 (FIG. 1) is configured, in response to the user input, to perform an action corresponding to the selected position on the representation of the chamber(s) of the heart 12. The action may include any one or more of the following: (a) generating a display of additional information about the selected position, for example, but not limited to, levels of electrical conductivity, a local activation time (LAT), and/or an MRI scan; (b) outputting a control command to perform an ablation at the selected position; (c) outputting a control command to perform further investigation at the selected position; and/or (d) adding annotations on the animated visualization 46 at the selected position.

The sources and sinks of the activation wavefront propagation path traces 42 may be annotated manually by the operator 16 (FIG. 1) or may be identified automatically by the system 10 (FIG. 1) and annotated automatically on the visualization 46 by the system 10.

Figure 6:
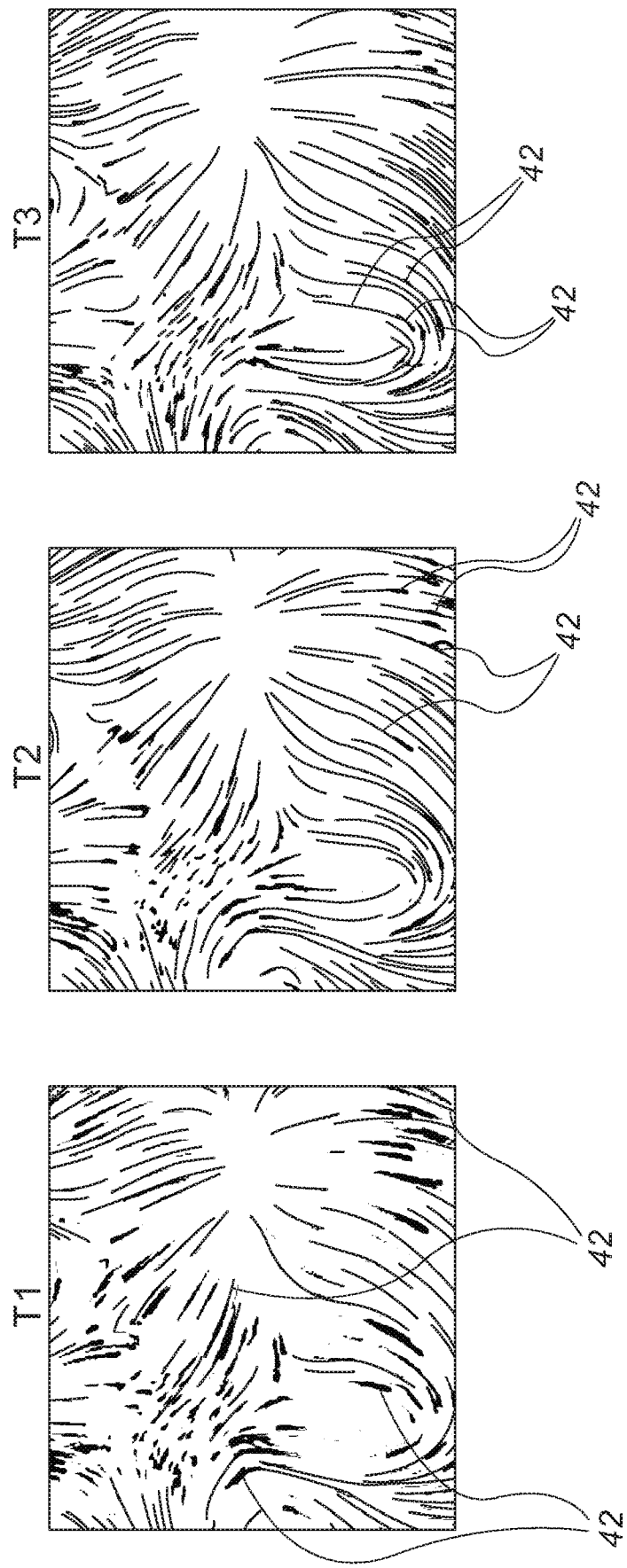
FIG. 6 is a view of the activation wavefront propagation path traces of a portion of the heart shown in FIGS. 3-5 at three different times.

Reference is now made to FIG. 6, which is a view of the electric-potential-flows 42 shown in FIGS. 3-5 at three different times (T1-T3) when the visualization 46 is animated for one portion of the heart 12. FIG. 6 illustrates the activation wavefront propagation path traces 42 growing by showing a single portion of the heart 12 at the three different times in a single figure.

Figures 7, 8:
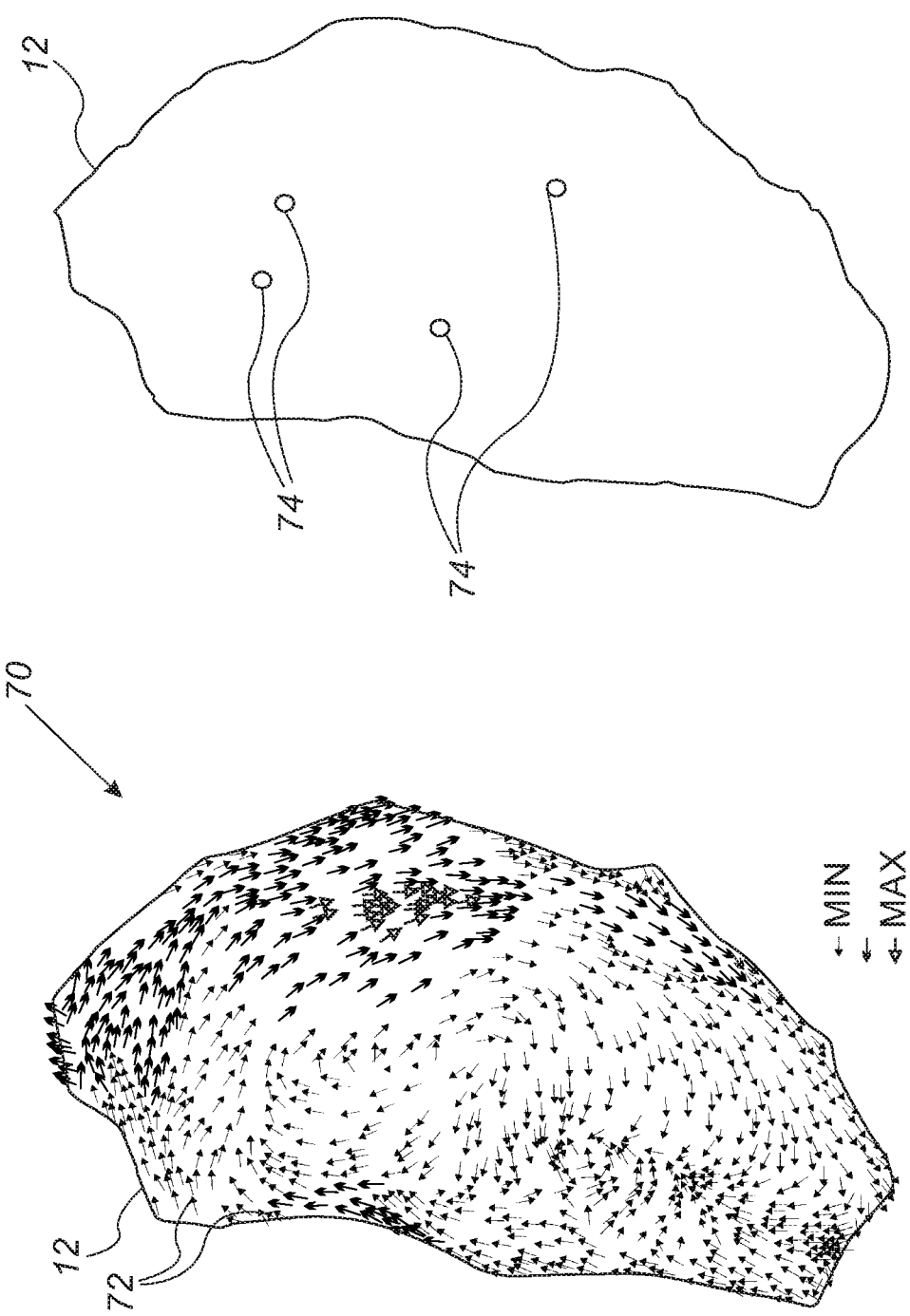
FIG. 7 is a view of a vector map generated by the system of FIG. 1 in accordance with an embodiment of the present invention.
FIG. 8 illustrates a plurality of random start locations of activation wavefront propagation path traces on the representation of the chamber(s) of the heart selected by the system of FIG. 1 in accordance with an embodiment of the present invention.

Reference is now made to FIG. 7, which is a view of a vector map 70 generated by the system 10 of FIG. 1 in accordance with an embodiment of the present invention. The processing circuitry 22 (FIG. 1) is configured to process electrical potentials captured by the probe 14 (FIG. 1) over time at multiple sample locations over the surface of the chamber(s) of the heart 12 to determine respective activation times at the multiple locations over the surface of the chamber(s) of the heart 12. It should be noted that the captured electric potentials may be exported by the processing circuitry 22 to a processor which is remote to the console 24 (FIG. 1), such as a processor of a PC or laptop, and processed in the remote processor for rendering on any suitable display screen.

The processing circuitry 22 is configured to prepare the vector map 70 including a plurality of velocity vectors 72 (only some labeled for the sake of simplicity) describing the propagation of activation wavefronts associated with the activation times. One method for preparing the vector map 70 is described in U.S. Pat. No. 6,301,496, which is herein incorporated by reference. Any suitable method for preparing the vector map 70 may also be used.

It should be noted that the description of the propagation of activation wavefronts used to prepare the visualization 46 may be derived from any suitable apparatus and by any suitable method. For example, body surface vests or any suitable medical examination device may be used using to estimate the activation wavefronts. Additionally, or alternatively, an inter-cardiac and/or trans-thoracic ultrasound-based system may be used to estimate mechanical wavefronts.

In the examples of FIGS. 8-13, the activation wavefront propagation path traces 42 are determined based on underlying velocity vectors from the vector map 70. However, the activation wavefront propagation path traces 42 may be calculated based on the description of the propagation of the activation wavefronts without the need to calculate the vector map 70.

Reference is now made to FIG. 8, which illustrates a plurality of random start locations 74 of activation wavefront propagation path traces 42 (FIGS. 2-6) on the representation of the chamber(s) of the heart 12 selected by the system 10 of FIG. 1 in accordance with an embodiment of the present invention. As part of an initialization process, the processing circuitry 22 (FIG. 1) is configured to select, in a random or a pseudo-random manner, the start locations 74 on the representation of the chamber(s) of the heart 12. Additionally, or alternatively, the start locations 74 may be selected according to a given pattern (e.g., a grid pattern), over the surface of the chamber(s) of the heart 12. A density of the start locations 74 may be user-configurable. Only some of the start locations 74 are shown in FIG. 8 for the sake of simplicity. The processing circuitry 22 is configured to assign the start locations 74 as start positions of the activation wavefront propagation path traces 42 (FIGS. 2-6) so that each activation wavefront propagation path trace 42 is assigned one start position 74.

Figure 11:
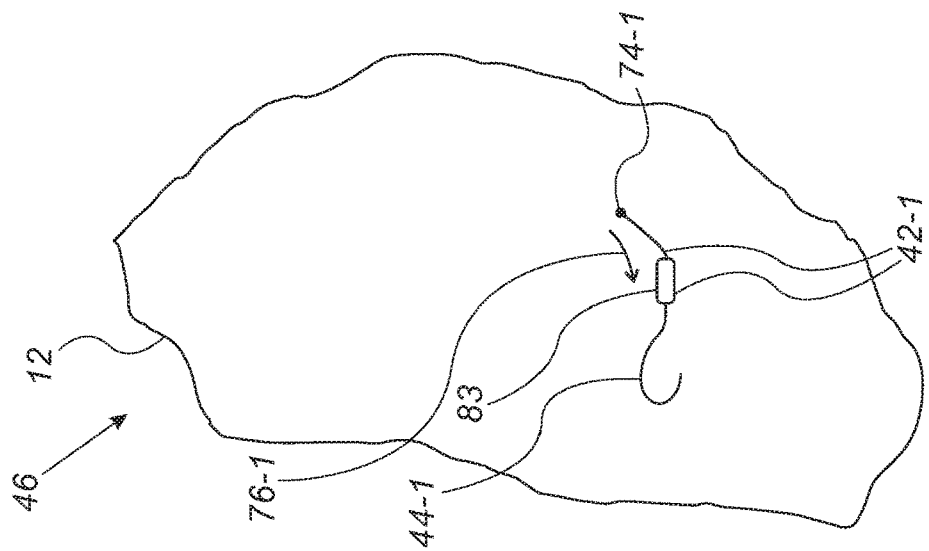
FIGS. 9-11 illustrate animation of the activation wavefront propagation path traces in accordance with an embodiment of the present invention.
Figure 10:
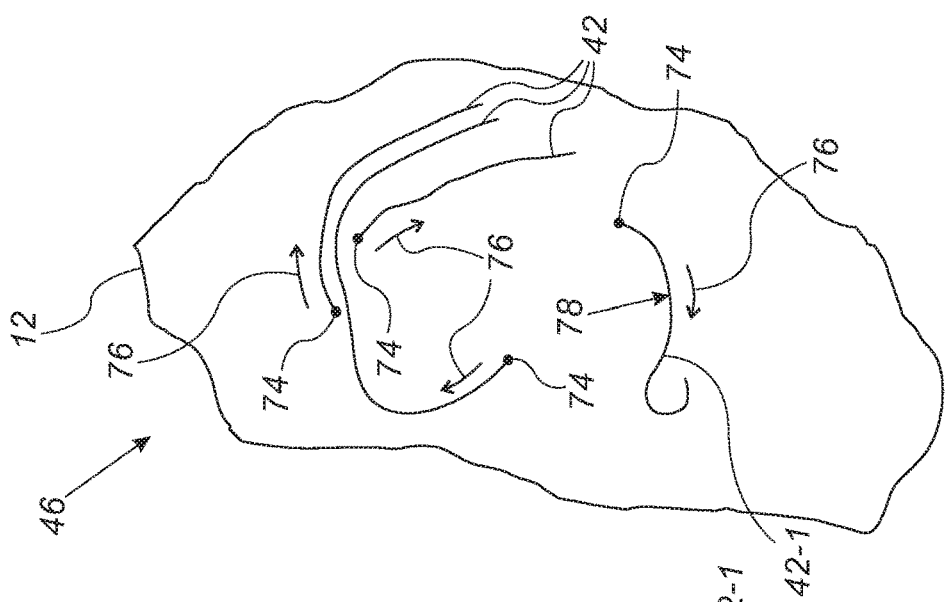
Figure 9:
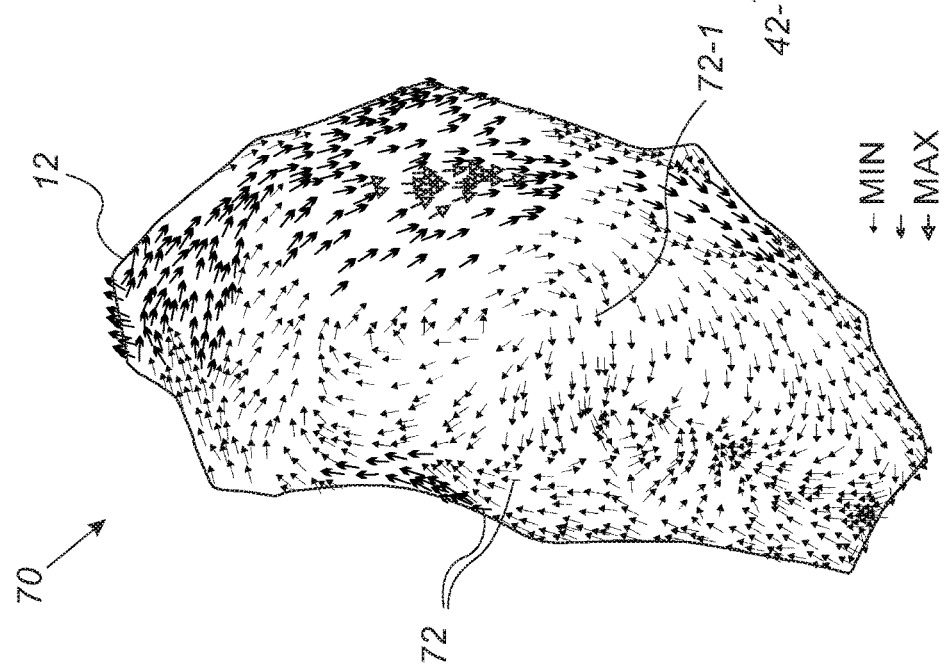

Reference is now made to FIGS. 9-11, which illustrate generation of the activation wavefront propagation path traces 42 in accordance with an embodiment of the present invention. FIG. 9 is a duplication of the vector map 70 of FIG. 7, which has been repeated here to aid understanding of FIGS. 10 and 11. FIG. 10 shows four activation wavefront propagation path traces 42 starting at their respective start locations 74 and continuing until an end-of-path is reached (e.g., based on a given time or a given distance). Arrows 76 show the direction in which the activation wavefront propagation path traces 42 grow when the visualization 46 is animated. It will be seen, by careful comparison to the velocity vectors 72 shown in FIG. 9 that the respective directions of the activation wavefront propagation path traces 42 shown in FIG. 10 are according to the underlying velocity vectors 72 of FIG. 9. For example, a direction of an activation wavefront propagation path trace 42-1 at a point 78 shown in FIG. 10 is determined by the direction of a vector 72-1 shown in FIG. 9. It should be noted that the velocity vector 72-1 does not describe a path of the propagation of the activation wavefront. The velocity vector 72-1 simply describes the velocity of the activation wavefront at a single point and does not describe any path of propagation.

FIG. 11 shows the growth of the activation wavefront propagation path trace 42-1 along a path 44-1 from a start location 74-1 in the direction shown by the arrow 76-1. FIG. 11 also shows that the activation wavefront propagation path trace 42-1 has a head 83 at its front, thereby indicating the direction in which the showing the activation wavefront propagation path trace 42-1 is growing.

Therefore, the processing circuitry 22 is configured to animate the growth of each activation wavefront propagation path trace 42 in the animated visualization 46 from its start position 74 to an end position. The processing circuitry 22 is generally configured to commence the animation of the growth of the activation wavefront propagation path traces 42 from their respective start positions 74 at substantially the same time. The processing circuitry 22 is generally configured, for each activation wavefront propagation path traces 42, to animate the growth of each activation wavefront propagation path traces 42 from its start position 74 to its end position in a cyclical manner. The processing circuitry 22 is configured to add a head indicator (e.g., the head 83) at the front of some, or all, activation wavefront propagation path traces 42, generally having a different format from the rest of the activation wavefront propagation path traces 42. The head indicator may be added whether the visualization 46 is animated or static. When the visualization 46 is animated, the processing circuitry 22 may be configured to fade each activation wavefront propagation path trace 42 over time and/or to remove one of the activation wavefront propagation path traces 42 when that activation wavefront propagation path trace 42 completes growing to the end of its path.

Non-conductive areas of the heart 12 may be of particular interest to a health professional. The processing circuitry 22 may be configured to add an indicator (e.g., a symbol and/or color) to the activation wavefront propagation path traces 42 to indicate a non-conductive area of the chamber(s) of the heart 12 in the visualization 46.

Figure 12:
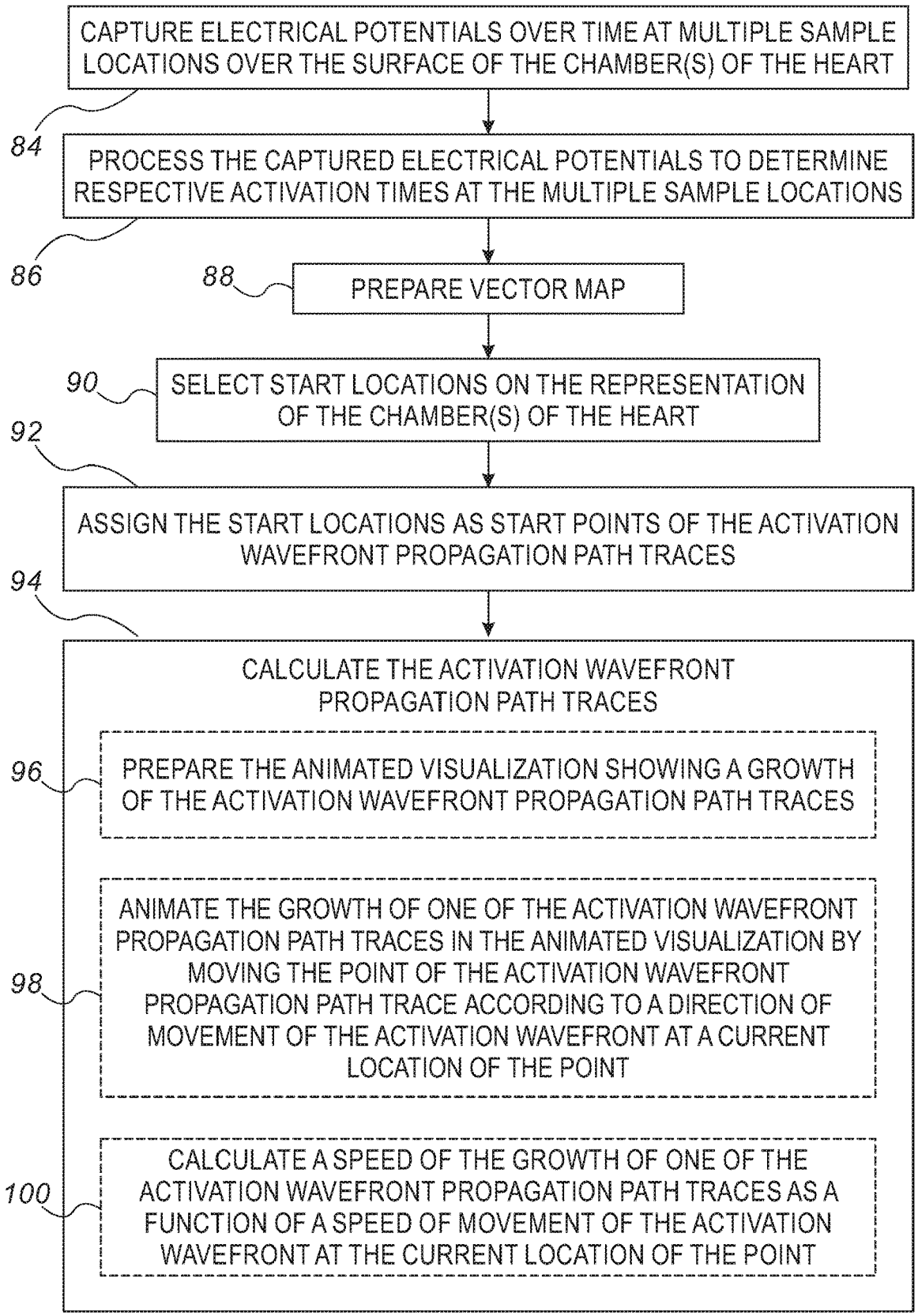
FIG. 12 is a flow chart showing exemplary steps in a method of operation of the system of FIG. 1.

Reference is now made to FIG. 12, which is a flow chart showing exemplary steps in a method of operation of the system 10 of FIG. 1. The steps of blocks 84-88 were described above with reference to FIGS. 1 and 7. As described above, steps 84-88 may be replaced by other data capture methods and/or other ways to describe the propagation of the activation wavefronts. The steps of blocks 90 and 92 were described above with reference to FIG. 8. The remainder of the blocks of FIG. 12 are now described in more detail below.

The processing circuitry 22 is configured to calculate (block 94) the activation wavefront propagation path traces 42. Each activation wavefront propagation path trace 42 describes a point on one activation wavefront being propagated over the surface of the chamber(s) of the heart according to an advancement of the activation wavefront. The activation wavefront propagation path traces 42 describe the propagation of different points according to corresponding activation wavefronts.

When the visualization 46 is an animated visualization, the processing circuitry 22 is operative to prepare (block 96)

the animated visualization showing a growth of the activation wavefront propagation path traces 42 on the representation of the chamber(s) of the heart according to the advancement of the activation wavefronts over the surface. The processing circuitry 22 is configured to animate (block 98) the growth of each one of the activation wavefront propagation path traces 42 in the animated visualization by moving the point of that activation wavefront propagation path trace 42 according to a direction of movement of the activation wavefront at a current location of the point being propagated. The processing circuitry 42 is configured to calculate (block 100) a speed of the growth of one of the activation wavefront propagation path traces 42 as a function of a speed of movement of the activation wavefront at the current location of the point being propagated.

In accordance with some embodiments, the processing circuitry 22 is configured to animate each activation wavefront propagation path trace 42 by moving the point of the activation wavefront propagation path trace 42 a first plurality of times according to a first direction and magnitude of a first vector of the plurality of velocity vectors 72 and then continuing moving the point of the activation wavefront propagation path trace a second plurality of times according to a second direction of a second vector of the plurality of velocity vectors 72.

In accordance with some embodiments, the propagation of the point may be calculated based on the following formula:

$L_N = L_c + \bar{v} \cdot \Delta t$, where $L_N$ is the next location of the point being propagated, $L_c$ is the current location of the point being propagated, $\bar{v}$ is a velocity vector from the description of the propagation of the activation wavefronts (e.g., from a function describing the propagation of the activation wavefronts) associated with the current location of the point and $\Delta t$ is a time value, which may be user configurable in order to increase and decrease the granularity of the movement of the point being propagated. When the visualization is animated, adjusting $\Delta t$ may be used to adjust the speed of the animation. $\Delta t$ may be any suitable value. For example, $\Delta t$ may be in the sub-millisecond (ms) range, e.g., 0.1 ms to 6 ms. The value of $\Delta t$ may be influenced by the range of the magnitudes of the velocity vectors 72. The value of $\Delta t$ could be user configurable or automatically set by the cardiac mapping system 10 to a suitable value, for example, but not limited to, 10% of the average velocity of the velocity vectors 72. Reducing the value of $\Delta t$ generally leads to a smoother, but slower, animation.

The processing circuitry 22 may be configured to assign a format (e.g., color, shading and/or pattern) and/or a size (e.g., length and/or width) to the activation wavefront propagation path traces 42 and/or the head indicator of the activation wavefront propagation path traces 42 in the animated visualization 46 (FIGS. 2-5) as a function of the speed of the activation wavefront at the current location of the point of one of the activation wavefront propagation path traces 42. For example, a darker color may indicate a point associated with a faster activation wavefront.

An example of an implementation of certain steps in the flow chart of FIG. 12 is now described with reference to FIG. 13, which is a view of a detailed illustration of an exemplary animation of the growth of one activation wavefront propagation path trace 42 in accordance with an embodiment of the present invention.

Figure 13:
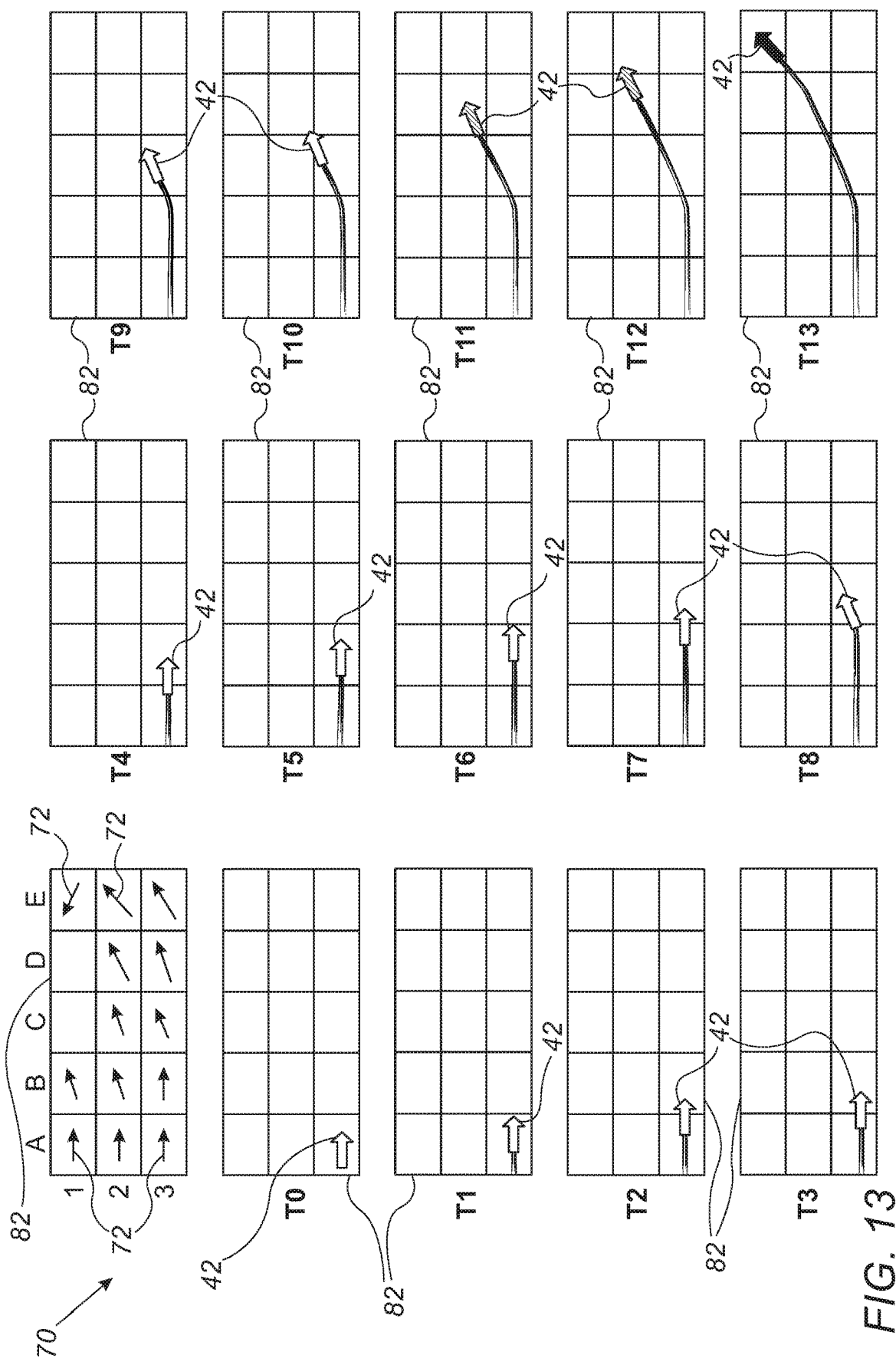
FIG. 13 is a view of a detailed illustration of an exemplary animation of one activation wavefront propagation path trace in accordance with an embodiment of the present invention.

The top left corner of FIG. 13 shows a grid 82 which represents a portion of the vector map 70 of FIG. 7 over a portion of the heart 12 (FIG. 7). For the sake of simplicity, the vector map 70 has been divided into rectangles. However, the vector map 70 may be divided using any suitable shapes which tessellate by themselves, such as triangles, squares and hexagons. In accordance with other embodiments the vector map 70 may be replaced with a function or other description describing the propagation of the activation wavefronts. For the sake of easy reference, each of the rectangles may be referenced by a column letter (A to E) and a row number (1 to 3). The vector map 70 includes velocity vectors 72 of which only some have been labeled for the sake of simplicity.

The grid 82 is duplicated thirteen times in FIG. 13 to show the extent of the activation wavefront propagation path trace 42 at various times, from time T0 to time T13.

FIG. 13 shows the start location of the activation wavefront propagation path trace 42 at time T0. The activation wavefront propagation path trace 42 then grows according to the corresponding velocity vectors 72 in the grid 82 over a time period from time T1 to time T13 as will now be described in more detail.

At time T0, the activation wavefront propagation path trace 42 is located in rectangle A3 of the grid 82 and therefore grows according to the direction and the magnitude of the velocity vector 72 located in rectangle A3 of the grid 82. At time T1, the activation wavefront propagation path trace 42 is still located in the rectangle A3 of the grid 82 and therefore grows again according to the direction and the magnitude of the velocity vector 72 located in rectangle A3 of the grid thereby moving the front of the activation wavefront propagation path trace 42 into the rectangle B3 at time T2.

From times T2 to T6, the front of the activation wavefront propagation path trace 42 is located in the rectangle B3. Therefore, the activation wavefront propagation path trace 42 grows according to the velocity vector 72 located in the rectangle B3.

It should be noted that the direction and size of the velocity vectors 72 in the rectangles A3 and B3 have the same direction and magnitude. Therefore, the activation wavefront propagation path trace 42 grows at a constant speed and direction across the rectangles A3 and B3.

From time T7 to T9, the front of the activation wavefront propagation path trace 42 is located in the rectangle C3. Therefore, the activation wavefront propagation path trace 42 grows according to the velocity vector 72 located in rectangle C3. It should be noted that the velocity vector 72 located in the rectangle C3 represents a change of direction with respect to the velocity vector 72 located in the rectangle B3.

At time T10, the front of the activation wavefront propagation path trace 42 is located in the rectangle D2. Therefore, the activation wavefront propagation path trace 42 now grows according to the direction and magnitude of the velocity vector 72 in rectangle D2. The velocity vector 72 in rectangle D2 is in the same direction as the velocity vector 72 of rectangle B3, but has a larger magnitude. Therefore, the activation wavefront propagation path trace 42 now grows faster, which is indicated by the distance travelled in one time period and a shading of the head 83 of the activation wavefront propagation path trace 42.

At time T11, the activation wavefront propagation path trace 42 still grows according to the velocity vector 72 of rectangle D2, thereby taking the front of the activation wavefront propagation path trace 42 into the rectangle E2 at time T12.

The velocity vector 72 of rectangle E2 is in a different direction to, and has a faster magnitude than, the velocity vector 72 of rectangle D2. Therefore, the activation wavefront propagation path trace 42 grows according to the direction and magnitude of the velocity vector 72 of rectangle D2 into rectangle E1 at time T13. It will be noted that the head 83 of the activation wavefront propagation path trace 42 now has a solid fill to indicate the faster speed.

The processing circuitry 22 (FIG. 1) determines to end activation wavefront propagation path trace 42 in rectangle E1 either because the activation wavefront propagation path trace 42 has a grown over a given distance or the activation wavefront propagation path trace 42 has grown for a time period equal to a given time period.

Additionally, it should be noted that the location of the front of the activation wavefront propagation path trace 42 has been used to determine which velocity vector 72 from the grid 82 should be used to determine direction and speed of growth. However, it will be appreciated that the location of any other part of the activation wavefront propagation path trace 42, e.g., the middle of the activation wavefront propagation path trace 42, may be used to determine which velocity vector 72 from the grid 82 should be used to determine growth.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The present invention is not limited by what has been particularly shown and described hereinabove. Rather the scope of the invention is defined by the appended claims and equivalents thereof.

What is claimed is:

1. A cardiac mapping system comprising:
 a medical examination device to capture data over time at multiple sample locations over a surface of at least one chamber of a heart;
 a display screen; and
 processing circuitry configured to:
  process the captured data to determine a description of a propagation of activation wavefronts associated with a plurality of activation times over the surface of the at least one chamber of the heart;
  calculate a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart according to an advancement of the one activation wavefront such that the plurality of activation wavefront propagation path traces describe the propagation of a plurality of different points according to corresponding ones of the activation wavefronts;
  prepare a visualization showing the plurality of activation wavefront propagation path traces on a representation of the at least one chamber of the heart, wherein the visualization is an animated visualization;
  prepare the animation showing a growth of the plurality of activation wavefront propagation path traces on the representation of the at least one chamber of the heart according to the advancement of the activation wavefronts over the surface;
  select, in a random or a pseudo-random manner, a plurality of start locations on the representation of the at least one chamber of the heart;
  assign the plurality of start locations as start positions of the plurality of activation wavefront propagation path traces from which to commence the respective activation wavefront propagation path traces, the one activation wavefront propagation path trace being assigned one start position of the start positions;
  animate the growth of each one activation wavefront propagation path trace of the plurality of activation wavefront propagation path traces from the one start position to an end position; and
  render the visualization to the display screen.

2. The system according to claim 1, wherein the processing circuitry is configured to animate the growth of the one activation wavefront propagation path trace in the animated visualization by moving the point of the one activation wavefront propagation path trace according to a direction of movement of the one activation wavefront at a current location of the point.

3. The system according to claim 1, wherein the processing circuitry is configured to calculate a speed of the growth of the one activation wavefront propagation path trace as a function of a speed of movement of the one activation wavefront at the current location of the point.

4. The system according to claim 1, wherein the processing circuitry is configured to commence the animation of the growth of the plurality of activation wavefront propagation path traces from the start positions at substantially a same time.

5. The system according to claim 1, wherein the processing circuitry is configured, for each one activation wavefront propagation path trace of the plurality of activation wavefront propagation path traces, to animate the one activation wavefront propagation path trace from the one start position to the end position in a cyclical manner.

6. The system according to claim 1, wherein the processing circuitry is configured to add a head indicator at the front of each one activation wavefront propagation path trace of the plurality of activation wavefront propagation path traces.

7. The system according to claim 1, wherein the processing circuitry is configured to add an indicator to one of the plurality of activation wavefront propagation path traces to indicate a non-conductive area of the at least one chamber of the heart.

8. The system according to claim 1, wherein the medical examination device is a probe configured to capture electrical potentials over time at the multiple sample locations over the surface of the at least one chamber of the heart.

9. The system according to claim 1, wherein the processing circuitry is configured to:
 prepare a vector map including a plurality of velocity vectors describing the propagation of the activation wavefronts;
 prepare an animated visualization showing a growth of the plurality of activation wavefront propagation path traces on the representation of the at least one chamber of the heart according to the advancement of the activation wavefronts over the surface; and
 animate each one activation wavefront propagation path trace of the plurality of activation wavefront propagation path traces by moving the point of the one activation wavefront propagation path trace a first plurality of times according to a first direction of a first vector of the plurality of velocity vectors and then continuing moving the point of the one activation wavefront a second plurality of times according to a second direction of a second vector of the plurality of velocity vectors.

10. A cardiac mapping method comprising:
capturing data over time at multiple sample locations over a surface of at least one chamber of a heart;
processing the captured data to determine a description of a propagation of activation wavefronts associated with a plurality of activation times over the surface of the at least one chamber of the heart;
calculating a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart according to an advancement of the one activation wavefront such that the plurality of activation wavefront propagation path traces describe the propagation of a plurality of different points according to corresponding ones of the activation wavefronts;
preparing a visualization showing the plurality of activation wavefront propagation path traces on a representation of the at least one chamber of the heart, wherein the visualization is an animated visualization;
preparing the animation showing a growth of the plurality of activation wavefront propagation path traces on the representation of the at least one chamber of the heart according to the advancement of the activation wavefronts over the surface;
selecting, in a random or a pseudo-random manner, a plurality of start locations on the representation of the at least one chamber of the heart;
assigning the plurality of start locations as start positions of the plurality of activation wavefront propagation path traces from which to commence the respective activation wavefront propagation path traces, the one activation wavefront propagation path trace being assigned one start position of the start positions;
animating the growth of each one activation wavefront propagation path trace of the plurality of activation wavefront propagation path traces from the one start position to an end position; and
rendering the visualization to a display screen.

11. The method according to claim 10, wherein the preparing the animated visualization includes moving the point of the one activation wavefront propagation path trace according to a direction of movement of the one activation wavefront at a current location of the point.

12. The method according to claim 10, further comprising calculating a speed of the growth of the one activation wavefront propagation path trace as a function of a speed of movement of the one activation wavefront at the current location of the point.

13. The method according to claim 10, further comprising commencing the animation of the growth of the plurality of activation wavefront propagation path traces from the start positions at substantially a same time.

14. The method according to claim 10, further comprising, for each one activation wavefront propagation path trace of the plurality of activation wavefront propagation path traces, animating the one activation wavefront propagation path trace from the one start position to the end position in a cyclical manner.

15. The method according to claim 10, further comprising adding a head indicator at the front of each one activation wavefront propagation path trace of the plurality of activation wavefront propagation path traces.

16. The method according to claim 10, further comprising adding an indicator to one of the plurality of activation wavefront propagation path traces to indicate a non-conductive area of the at least one chamber of the heart.

17. The method according to claim 10, further comprising:
preparing a vector map including a plurality of velocity vectors describing the propagation of the activation wavefronts;
preparing an animated visualization showing a growth of the plurality of activation wavefront propagation path traces on the representation of the at least one chamber of the heart according to the advancement of the activation wavefronts over the surface; and
animating each one activation wavefront propagation path trace of the plurality of activation wavefront propagation path traces by moving the point of the one activation wavefront propagation path trace a first plurality of times according to a first direction of a first vector of the plurality of velocity vectors and then continuing moving the point of the one activation wavefront a second plurality of times according to a second direction of a second vector of the plurality of velocity vectors.

18. A cardiac visualization system comprising:
a memory to store a description of a propagation of activation wavefronts associated with a plurality of activation times over a surface of at least one chamber of a heart; and
processing circuitry configured to:
process the captured data to determine a description of a propagation of activation wavefronts associated with a plurality of activation times over the surface of the at least one chamber of the heart;
calculate a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart according to an advancement of the one activation wavefront such that the plurality of activation wavefront propagation path traces describe the propagation of a plurality of different points according to corresponding ones of the activation wavefronts;
prepare a visualization showing the plurality of activation wavefront propagation path traces on a representation of the at least one chamber of the heart, wherein the visualization is an animated visualization;
prepare the animation showing a growth of the plurality of activation wavefront propagation path traces on the representation of the at least one chamber of the heart according to the advancement of the activation wavefronts over the surface;
select, in a random or a pseudo-random manner, a plurality of start locations on the representation of the at least one chamber of the heart;
assign the plurality of start locations as start positions of the plurality of activation wavefront propagation path traces from which to commence the respective activation wavefront propagation path traces, the one activation wavefront propagation path trace being assigned one start position of the start positions;
animate the growth of each one activation wavefront propagation path trace of the plurality of activation wavefront propagation path traces from the one start position to an end position; and
render the visualization to a display screen.

19. The system according to claim 18, wherein the processing circuitry is configured to animate the growth of the one activation wavefront propagation path trace in the animated visualization by moving the point of the one activation wavefront propagation path trace according to a direction of movement of the one activation wavefront at a current location of the point.

20. The system according to claim 18, wherein the processing circuitry is configured to calculate a speed of the growth of the one activation wavefront propagation path trace as a function of a speed of movement of the one activation wavefront at the current location of the point.

21. A cardiac visualization method comprising:
storing a description of a propagation of activation wavefronts associated with a plurality of activation times over a surface of at least one chamber of a heart;
processing the captured data to determine a description of a propagation of activation wavefronts associated with a plurality of activation times over the surface of the at least one chamber of the heart;
calculating a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart according to an advancement of the one activation wavefront such that the plurality of activation wavefront propagation path traces describe the propagation of a plurality of different points according to corresponding ones of the activation wavefronts;
preparing a visualization showing the plurality of activation wavefront propagation path traces on a representation of the at least one chamber of the heart, wherein the visualization is an animated visualization;
preparing the animation showing a growth of the plurality of activation wavefront propagation path traces on the representation of the at least one chamber of the heart according to the advancement of the activation wavefronts over the surface;
selecting, in a random or a pseudo-random manner, a plurality of start locations on the representation of the at least one chamber of the heart;
assigning the plurality of start locations as start positions of the plurality of activation wavefront propagation path traces from which to commence the respective activation wavefront propagation path traces, the one activation wavefront propagation path trace being assigned one start position of the start positions;
animating the growth of each one activation wavefront propagation path trace of the plurality of activation wavefront propagation path traces from the one start position to an end position; and
rendering the visualization to a display screen.

22. The method according to claim 21, further comprising animating the growth of the one activation wavefront propagation path trace in the animated visualization by moving the point of the one activation wavefront propagation path trace according to a direction of movement of the one activation wavefront at a current location of the point.

23. The method according to claim 21, further comprising calculating a speed of the growth of the one activation wavefront propagation path trace as a function of a speed of movement of the one activation wavefront at the current location of the point.

24. A software product, comprising a non-transient computer-readable medium in which program instructions are stored, which instructions, when read by a central processing unit (CPU), cause the CPU to:
store a description of a propagation of activation wavefronts associated with a plurality of activation times over a surface of at least one chamber of a heart;
process the captured data to determine a description of a propagation of activation wavefronts associated with a plurality of activation times over the surface of the at least one chamber of the heart;
calculate a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart according to an advancement of the one activation wavefront such that the plurality of activation wavefront propagation path traces describe the propagation of a plurality of different points according to corresponding ones of the activation wavefronts;
prepare a visualization showing the plurality of activation wavefront propagation path traces on a representation of the at least one chamber of the heart, wherein the visualization is an animated visualization;
prepare the animation showing a growth of the plurality of activation wavefront propagation path traces on the representation of the at least one chamber of the heart according to the advancement of the activation wavefronts over the surface;
select, in a random or a pseudo-random manner, a plurality of start locations on the representation of the at least one chamber of the heart;
assign the plurality of start locations as start positions of the plurality of activation wavefront propagation path traces from which to commence the respective activation wavefront propagation path traces, the one activation wavefront propagation path trace being assigned one start position of the start positions;
animate the growth of each one activation wavefront propagation path trace of the plurality of activation wavefront propagation path traces from the one start position to an end position; and
render the visualization to the display screen.

25. A cardiac mapping system comprising:
a medical examination device to capture data over time at multiple sample locations over a surface of at least one chamber of a heart;
a display screen; and
processing circuitry configured to:
process the captured data to determine a description of a propagation of activation wavefronts associated with a plurality of activation times over the surface of the at least one chamber of the heart;
calculate a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart according to an advancement of the one activation wavefront such that the plurality of activation wavefront propagation path traces describe the propagation of a plurality of different points according to corresponding ones of the activation wavefronts;

prepare a vector map including a plurality of velocity vectors describing the propagation of the activation wavefronts;

prepare an animated visualization showing the plurality of activation wavefront propagation path traces on a representation of the at least one chamber of the heart according to the advancement of the activation wavefronts over the surface;

animate each one activation wavefront propagation path trace of the plurality of activation wavefront propagation path traces by moving the point of the one activation wavefront propagation path trace a first plurality of times according to a first direction of a first vector of the plurality of velocity vectors and then continuing moving the point of the one activation wavefront a second plurality of times according to a second direction of a second vector of the plurality of velocity vectors; and render the visualization to the display screen.

26. A cardiac mapping method comprising:

capturing data over time at multiple sample locations over a surface of at least one chamber of a heart;

processing the captured data to determine a description of a propagation of activation wavefronts associated with a plurality of activation times over the surface of the at least one chamber of the heart;

calculating a plurality of activation wavefront propagation path traces wherein each one activation wavefront propagation path trace of the plurality of activation wavefront propagation path traces describes a point on one activation wavefront of the activation wavefronts being propagated over the surface of the at least one chamber of the heart according to an advancement of the one activation wavefront such that the plurality of activation wavefront propagation path traces describe the propagation of a plurality of different points according to corresponding ones of the activation wavefronts;

preparing a vector map including a plurality of velocity vectors describing the propagation of the activation wavefronts;

preparing a visualization showing the plurality of activation wavefront propagation path traces on a representation of the at least one chamber of the heart according to the advancement of the activation wavefronts over the surface;

animating each one activation wavefront propagation path trace of the plurality of activation wavefront propagation path traces by moving the point of the one activation wavefront propagation path trace a first plurality of times according to a first direction of a first vector of the plurality of velocity vectors and then continuing moving the point of the one activation wavefront a second plurality of times according to a second direction of a second vector of the plurality of velocity vectors; and rendering the visualization to a display screen.

* * * * *